(12) United States Patent
Loman

(10) Patent No.: US 9,335,241 B2
(45) Date of Patent: May 10, 2016

(54) MONITORING CAPSULE CONFIGURED FOR MEASURING A PROPERTY OF A FLUID WITHIN A VESSEL

(71) Applicant: GM GLOBAL TECHNOLOGY OPERATIONS LLC, Detroit, MI (US)

(72) Inventor: Jerry D. Loman, Clinton Township, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 274 days.

(21) Appl. No.: 14/051,608

(22) Filed: Oct. 11, 2013

(65) Prior Publication Data

US 2015/0101408 A1    Apr. 16, 2015

(51) Int. Cl.
*G01N 9/12* (2006.01)
(52) U.S. Cl.
CPC .......................................... *G01N 9/12* (2013.01)
(58) Field of Classification Search
CPC .................................... G01N 9/14; G01N 9/12
See application file for complete search history.

(56) References Cited

U.S. PATENT DOCUMENTS

| | | | | |
|---|---|---|---|---|
| 2,198,351 A | * | 4/1940 | Thielers | G01N 9/00 200/190 |
| 3,661,652 A | * | 5/1972 | Uitenbroek | G01N 9/18 429/10 |
| 4,000,657 A | * | 1/1977 | Ponsar | G01N 9/12 422/613 |
| 4,061,839 A | * | 12/1977 | Kohler | H01M 10/484 429/93 |
| 5,900,547 A | * | 5/1999 | Bartkiewicz | G01N 9/18 73/32 R |
| 2001/0029782 A1 | * | 10/2001 | Articolo | G01F 23/0038 73/314 |

* cited by examiner

*Primary Examiner* — Hezron E Williams
*Assistant Examiner* — Mark A Shabman
(74) *Attorney, Agent, or Firm* — Quinn Law Group, PLLC

(57) ABSTRACT

A monitoring system is configured for monitoring a property of a fluid. The monitoring system includes a vessel and a monitoring capsule. The vessel is configured for holding a volume of the fluid therein. The monitoring capsule is configured for disposition within the vessel. The monitoring capsule includes a housing, a hydrometer, and a sensor. The hydrometer is movably disposed within the housing. The hydrometer is configured to measure the property of the fluid. The sensor is operatively attached to the housing and configured to sense the measured property of the fluid.

15 Claims, 2 Drawing Sheets

MONITORING CAPSULE CONFIGURED FOR MEASURING A PROPERTY OF A FLUID WITHIN A VESSEL

TECHNICAL FIELD

The present disclosure relates to a monitoring capsule configured for measuring a property of a fluid within a vessel.

BACKGROUND

Vehicles include fluid reservoirs that contain a fluid, such as washer fluid, oil, gasoline, engine coolant, and the like. Vehicle windshield washer systems typically include a washer fluid reservoir mounted in the engine compartment. A motor-driven pump typically draws washer fluid from the reservoir and pumps the washer fluid under pressure to spray nozzles in the vicinity of the windshield to spray the washer fluid over the windshield. During inclement weather, rain or snow may accumulate on the windshield.

SUMMARY

A monitoring capsule is disclosed herein that is configured for measuring a property of a fluid within a vessel. The monitoring capsule includes a housing, a hydrometer, and a sensor. The hydrometer is movably disposed within the housing. The hydrometer is configured to measure the property of the fluid. The sensor is operatively attached to the housing and configured to sense the measured property of the fluid.

In another aspect of the disclosure, a monitoring system is configured for monitoring a property of a fluid. The monitoring system includes a vessel and a monitoring capsule. The vessel is configured for holding a volume of the fluid therein. The monitoring capsule is configured for disposition within the vessel. The monitoring capsule includes a housing, a hydrometer, and a sensor. The hydrometer is movably disposed within the housing. The hydrometer is configured to measure the property of the fluid. The sensor is operatively attached to the housing and configured to sense the measured property of the fluid.

A vehicle is disclosed in yet another aspect of the disclosure. The vehicle includes a vessel, a monitoring capsule, and a receiver. The vessel is configured for holding a volume of the fluid therein. The monitoring capsule is configured for disposition within the vessel. The monitoring capsule includes a housing, a hydrometer, a sensor, and a transmitter. The hydrometer is movably disposed within the housing. The hydrometer is configured to measure the property of the fluid. The sensor is operatively attached to the housing and is configured to sense the measured property of the fluid. The transmitter is operatively connected to the sensor and is configured for transmitting a signal corresponding to the measured property of the fluid. The receiver is configured for receiving the signal from the transmitter.

The above features and advantages and other features and advantages of the present disclosure are readily apparent from the following detailed description of the best modes for carrying out the disclosure when taken in connection with the accompanying drawings.

DESCRIPTION OF THE PREFERRED EMBODIMENTS

Figure 1:
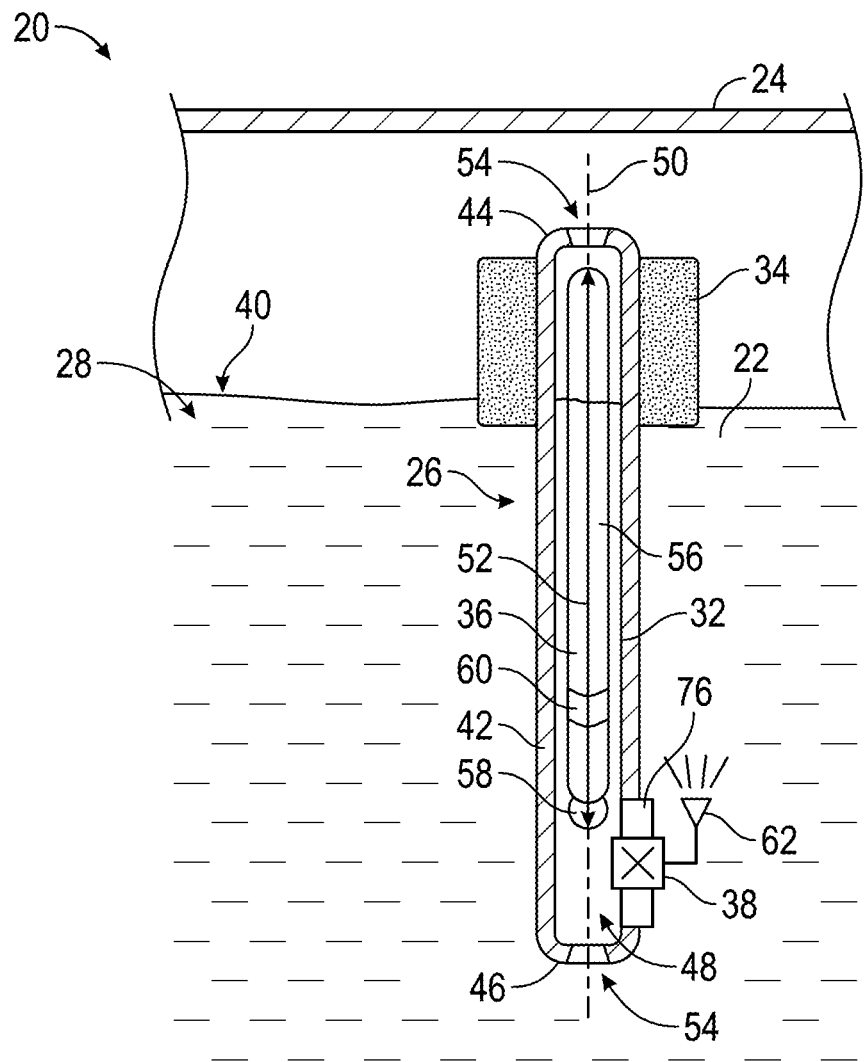
FIG. 1 is a schematic partial cross-sectional view of a monitoring system including a monitoring capsule floating in a volume of fluid within a vessel.

Referring to the Figures, wherein like numerals indicate like parts throughout the several views, a monitoring system is generally shown at 20 in FIG. 1. The monitoring system 20 is configured for monitoring a property of a fluid 22. The property may include the specific gravity, American Petroleum Institute (API) gravity, and the like.

Figure 3:
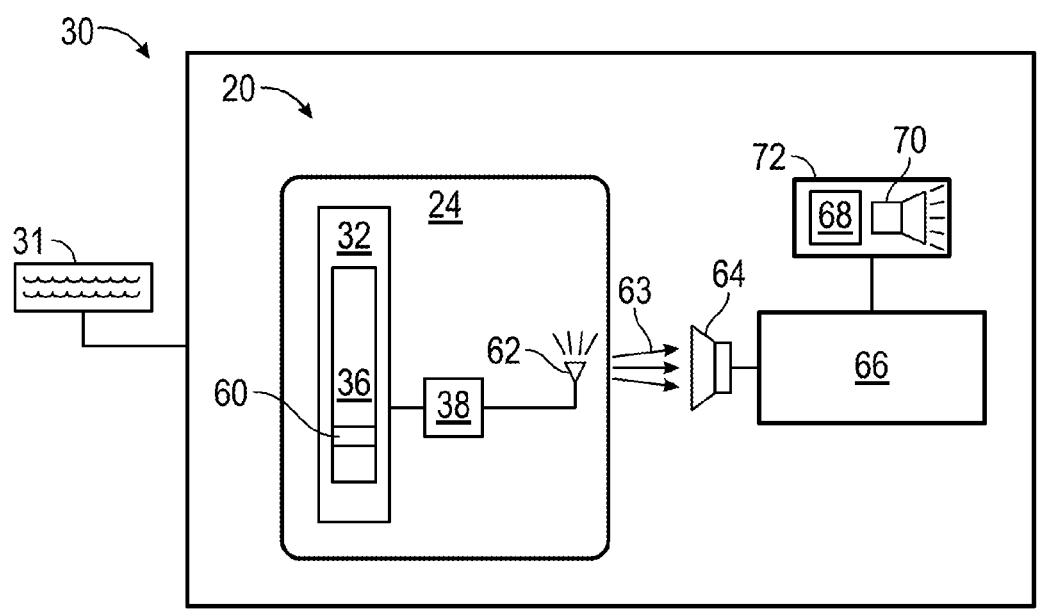
FIG. 3 is a schematic diagrammatic view of the monitoring system disposed within a vehicle, where the monitoring system includes a controller in communication with a visual display and an auditory signal.

The monitoring system 20 includes a vessel 24 and a monitoring capsule 26. The vessel 24 is configured for holding a volume 28 of the fluid 22 therein. The vessel 24 may be configured to hold fluids 22, such as windshield washer solvent, engine coolant, oil, gasoline, kerosene, paint, and the like. Referring to FIG. 3, the vessel 24 may be used within a vehicle 30 having at least one wheel 31. It should be appreciated that the vessel 24 is not limited to being used within a vehicle 30, but may be used elsewhere, including a boat, motorcycle, and the like. Alternatively, the vessel 24 may be a cargo container or vat filled with fluid 22 to be monitored.

Referring again to FIG. 1, the monitoring capsule 26 is configured to be disposed within the vessel 24. The monitoring capsule 26 includes a housing 32, an orientation device 34, a hydrometer 36, and a sensor 38. The orientation device 34 may be operatively attached to the housing 32 and is configured to orient the housing 32, relative to the fluid 22, within the vessel 24. More specifically, the orientation device 34 may be configured to float within the fluid 22 such that the housing 32 is generally upright, relative to a surface 40 of the fluid 22. In one non-limiting example, the orientation device 34 may include buoyant foam such as a foamed plastic and the like. As such, the orientation device 34 floats within the fluid 22, causing the orientation device 34 to be orientated in an upright position, relative to the surface 40 of the fluid 22.

The housing 32 includes a wall 42 that extends between a first end 44 and a second end 46. The wall 42 surrounds a passage 48 that extends along an axis 50 between the first end 44 and the second end 46. The hydrometer 36 extends along a length 52 and is movably disposed within the passage 48. The passage 48 may be any size and shape that allows the hydrometer 36 to move along the axis 50, relative to the first end 44 and the second end 46, without the length 52 of the hydrometer 36 diverging from the axis 50. In a non-limiting example, the passage 48 may be cylindrical. The housing 32 defines at least one opening 54 to the passage 48, which allows the fluid 22 to enter the passage 48. Referring to FIG. 1, the housing 32 defines two openings 54. As such, the first end 44 and the second end 46 each define an opening 54 that is sized to allow fluid 22 to enter the passage 48, while preventing the hydrometer 36 from leaving the passage 48. The orientation device 34 may be operatively attached to the housing 32, proximate the first end 44, to ensure the housing 32 floats in the upright position, relative to the surface 40 of the fluid 22.

The hydrometer 36 is configured to measure the property of the fluid 22. By way of a non-limiting example, the hydrometer 36 may be configured to measure the specific gravity or relative density of fluids 22; that is the ratio of the density of the fluid 22 to the density of water. As such, the hydrometer 36 may be configured to determine the alcohol content of windshield washer solvent, engine coolant, oil, gasoline, kerosene, paint, and the like. The hydrometer 36 may be made of glass. The hydrometer 36 may include a cylindrical stem 56 and a bulb 58 weighted with mercury, lead shot, and the like to make the hydrometer 36 float upright in the fluid 22. Since the hydrometer 36 is movably disposed within the passage 48 of the housing 32, when the monitoring capsule 26 is disposed in the fluid 22, the hydrometer 36 is configured to float upright within the housing 32, relative to the surface 40 of the fluid 22, as a function of the measured specific gravity or relative density of the fluid 22. As will be explained in more detail below, at least one indicator 60 is disposed along the stem 56. The indicator 60 corresponds to a specific gravity. Therefore, the lower the density of the fluid 22, the more the hydrometer 36 will tend to sink, relative to the surface 40 of the fluid 22 and the first end 44 of the housing 32.

The indicator 60 may include a magnet that is disposed on the stem 56 at a location corresponding to a specific gravity. The location of the indicator 60 along the stem correlates to a particular specific gravity which may therefore be calibrated to correspond to a particular amount of alcohol in the fluid 22. By way of a non-limiting example, the location of the indicator 60 may correspond to an upper or lower limit of the amount of alcohol in the fluid 22. In another non-limiting example, the location of the indicator 60 may correspond to a desired amount of alcohol in the fluid 22. As yet another non-limiting example, a plurality of indicators 60 may be disposed on the stem 56, where each indicator 60 corresponds to a discrete specific gravity of the fluid 22.

The sensor 38 is operatively attached to the housing 32. The sensor 38 may be a Hall effect sensor 38. It should be appreciated that other sensors 38 may also be used. In one non-limiting example, the sensor 38 is configured to sense the measured specific gravity of the fluid 22, based on the proximity of the indicator 60 to the sensor 38. As previously discussed, the specific gravity of the fluid 22 would correspond to an amount of alcohol contained within the fluid 22. The Hall effect sensor 38 is configured to sense a proximity of the magnet, via the magnetic field, as the hydrometer 36 floats along the axis 50 within the fluid 22, relative to the first end 44 and the second end 46 of the housing 32.

Figure 2:
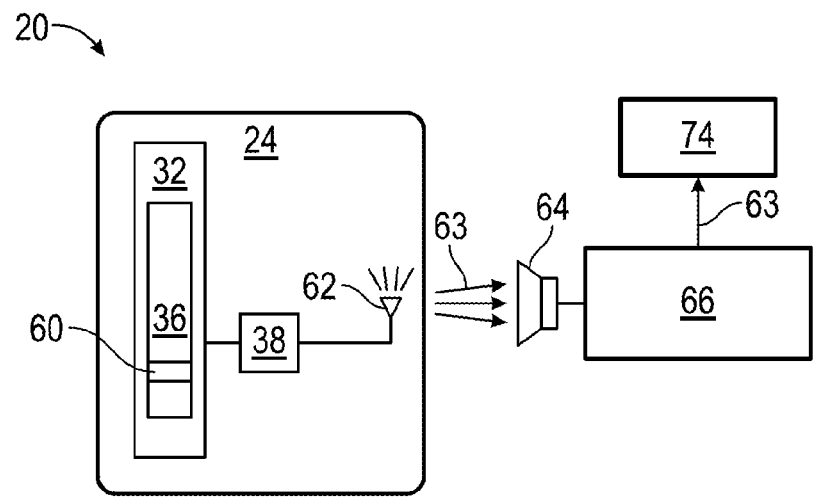
FIG. 2 is a schematic diagrammatic view of the monitoring system including a controller and a telemetry sensing system.

Referring to FIGS. 1-3, the monitoring system 20 may also include a transmitter 62 that is operatively connected to the sensor 38. The transmitter 62 may be a radio frequency (RF) transmitter 62. As such, the transmitter 62 is configured to send a signal 63 to indicate a condition of the fluid 22. The condition of the fluid 22 may be that the alcohol content is too high or too low. Alternatively, the transmitter 62 may be configured to send a signal 63 indicating the actual alcohol content of the fluid 22. The signal 63 may be sent to a receiver 64. The receiver 64 may process the signal 63 and, in turn, activate an alert as to the condition of the fluid 22. Within the vehicle 30, the receiver 64 may be included as part of a controller 66, such as a body control module (BCM), an engine control module (ECM), and the like. The alert may illuminate a visual display 68 and/or activate an auditory signal 70 indicating the condition of the fluid 22. Within the vehicle 30, the display may be a light that illuminates on a dashboard 72. Alternatively, referring to FIG. 2, the signal 63 may, in turn, be sent to a telemetry sensing system 74, including, but not limited to an OnStar® service system, to manage on-board vehicle 30 fluid maintenance. As such, an operator of the vehicle 30 may be able to remotely check the condition of the fluid 22.

Referring again to FIG. 1, the monitoring system 20 may also include a magnetic shunt 76 operatively attached to the sensor 38. The magnetic shunt 76 is configured to insulate the sensor 38 from magnetic interference. The magnetic shunt 76 includes an inductor that functions as a choke formed on a toroidal core from a low-retentivity material. At least two windings permeated by line current may be wound on the core and a magnetically conductive material may be disposed in the proximity of the choke.

While the best modes for carrying out the disclosure have been described in detail, those familiar with the art to which this disclosure relates will recognize various alternative designs and embodiments for practicing the disclosure within the scope of the appended claims.

The invention claimed is:

1. A monitoring capsule configured for measuring a property of a fluid within a vessel, the monitoring capsule comprising:
   a hydrometer including a stem and bulb extending from the stem;
   a housing including a wall extending between a first end and a second end;
   wherein the wall defines a tubular passage and the hydrometer is movably disposed within the passage;
   wherein the first end and the second end each define an opening sized to allow fluid to enter the passage;
   an orientation device operatively attached to the housing, proximate the first end, wherein the orientation device is configured to float within the fluid;
   wherein the hydrometer is movably disposed within the housing with the stem disposed between the bulb and the first end such that the bulb is operatively disposed in spaced relationship to the orientation device;
   wherein the bulb is weighted such that the hydrometer floats upright, relative to a surface of the fluid;
   wherein the hydrometer is configured to measure the property of the fluid; and
   a sensor operatively attached to the housing and configured to sense the measured property of the fluid.

2. A monitoring capsule, as set forth in claim 1 further comprising an indicator operatively disposed on the hydrometer;
   wherein the sensor is configured to sense the measured property of the fluid as a function of a proximity of the indicator to the sensor.

3. A monitoring capsule, as set forth in claim 1, wherein the sensor is a Hall effect sensor.

4. A monitoring capsule, as set forth in claim 3, wherein the hydrometer includes a magnet;
   wherein the Hall effect sensor is configured to sense a proximity of the magnet.

5. A monitoring capsule, as set forth in claim 1, further comprising a magnetic shunt operatively attached to the sensor;
   wherein the magnetic shunt is configured to insulate the sensor from magnetic interference.

6. A monitoring system configured for monitoring a property of a fluid, the system comprising:
   a vessel configured for holding a volume of the fluid therein;
   a monitoring capsule configured for disposition within the vessel, the monitoring capsule including:
      a hydrometer including a stem and bulb extending from the stem;
      a housing including a wall extending between a first end and a second end;

wherein the wall defines a tubular passage and the hydrometer is movably disposed within the passage;

wherein the first end and the second end each define an opening sized to allow fluid to enter the passage;

an orientation device operatively attached to the housing, proximate the first end, wherein the orientation device is configured to float within the fluid;

wherein the hydrometer is movably disposed within the housing with the stem disposed between the bulb and the first end such that the bulb is operatively disposed in spaced relationship to the orientation device;

wherein the bulb is weighted such that the hydrometer floats upright, relative to a surface of the fluid;

wherein the hydrometer is configured to measure the property of the fluid; and a sensor operatively attached to the housing and configured to sense the measured property of the fluid.

7. A system, as set forth in claim 6, further comprising an indicator operatively disposed on the hydrometer;

wherein the sensor is configured to sense the measured property of the fluid as a function of a proximity of the indicator to the sensor.

8. A system, as set forth in claim 6, wherein the sensor is a Hall effect sensor.

9. A system, as set forth in claim 8, wherein the hydrometer includes a magnet;

wherein the Hall effect sensor is configured to sense a proximity of the magnet.

10. A monitoring system, as set forth in claim 6, further comprising a transmitter operatively connected to the sensor and configured for transmitting a signal corresponding to the measured property of the fluid.

11. A monitoring system, as set forth in claim 10, further comprising a magnetic shunt operatively attached to the sensor;

wherein the magnetic shunt is configured to insulate the sensor from magnetic interference.

12. A monitoring system, as set forth in claim 10, wherein the transmitter is a radio frequency transmitter.

13. A vehicle comprising:

a vessel configured for holding a volume of the fluid therein;

a monitoring capsule configured for disposition within the vessel, the monitoring capsule including:

a hydrometer including a stem and bulb extending from the stem;

a housing including a wall extending between a first end and a second end;

wherein the wall defines a tubular passage and the hydrometer is movably disposed within the passage;

wherein the first end and the second end each define an opening sized to allow fluid to enter the passage;

an orientation device operatively attached to the housing, proximate the first end, wherein the orientation device is configured to float within the fluid;

wherein the hydrometer is movably disposed within the housing with the stem disposed between the bulb and the first end such that the bulb is operatively disposed in spaced relationship to the orientation device;

wherein the bulb is weighted such that the hydrometer floats upright, relative to a surface of the fluid;

wherein the hydrometer is configured to measure the property of the fluid;

a sensor operatively attached to the housing and configured to sense the measured property of the fluid; and a transmitter operatively connected to the sensor and configured for transmitting a signal corresponding to the measured property of the fluid; and a receiver configured for receiving the signal from the transmitter.

14. A vehicle, as set forth in claim 13, wherein the transmitter is a radio frequency transmitter.

15. A vehicle, as set forth in claim 13, further comprising a magnetic shunt operatively attached to the sensor;

wherein the magnetic shunt is configured to insulate the sensor from magnetic interference.

* * * * *